Feb. 14, 1950 L. W. SHERWOOD Plant Pat. 924
PEACH TREE
Filed Feb. 25, 1948
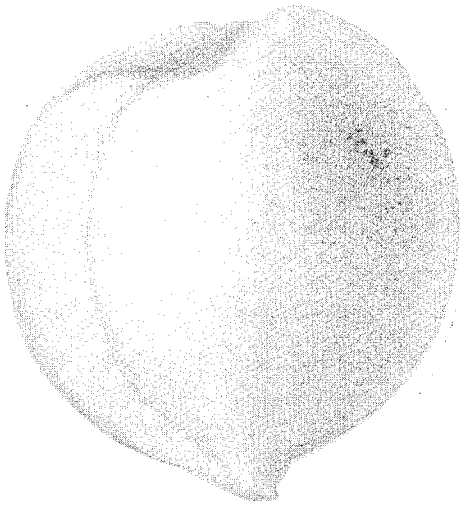
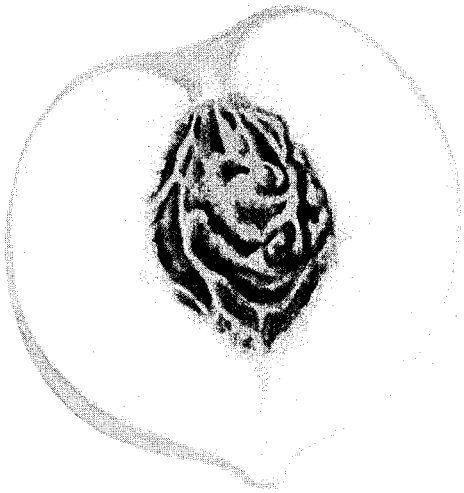
INVENTOR
Lawrence W. Sherwood
By Orville M. Kile
PLANT PATENT AGENT Patented Feb. 14, 1950

Plant Pat. 924

UNITED STATES PATENT OFFICE

924

PEACH TREE

Lawrence W. Sherwood, Fullerton, Calif.

Application February 25, 1948, Serial No. 10,781

1 Claim. (Cl. 47—62)

My present discovery relates to a new and distinct variety of peach tree producing fruit of the white freestone type. The tree is a very heavy bearer and comes into bearing early. The fruit matures late, resembles Hale in size and shape, has a distinctive and slightly tart flavor, and keeps exceptionally well. Both texture and flavor of the fruit are excellent.

This variety originated as a chance seedling of unknown parentage. The seed from which it grew may have been dropped by a bird or animal. I first observed the tree growing on a neighbor's property at the time I was doing some work on some other orchard trees. The owner evidenced no interest in the possible value of the variety, so with his permission I obtained some buds and propagated the new variety in my orchards at Fullerton. I have since been observing it and making further propagations.

This variety has proved to be a very unusual variety, one of the outstanding features being the longevity of the tree. The mother tree was probably 5 or 6 years old when I first discovered it in 1930 and is still healthy and more vigorous than the average tree of a similar age growing under similar conditions. Its vigor indicates that it should remain commercially profitable for many more years.

The asexually reproduced trees have reproduced fruit identical to that of the mother tree in every respect, and characteristics of the tree itself appear to be identical to those of the mother tree.

Accompanying illustrations show in approximately true colors, a side view and cross-section view of a typical specimen of the fruit of this new variety.

Following is a detailed description of the principal features of this new peach variety. Color plate numbers refer to Ridgway's Color Standards and Nomenclature.

*The tree*

Growth: Very vigorous and dense; drooping.
Form: Round-topped; stocky.
Trunk: Smooth.
Branches: Very pronounced brownish-red color, especially the new wood and fruiting twigs. Lenticles many, average size and of reddish color.
Leaves:
- *Size.*—Quite large. Medium width but very long, averaging about 1 inch wide and 6 inches long.
- *Quantity.*—Many to a single branch.

- *Color.*—Rich green, with rib ivory white.
- *Petiole.*—Short and thick.
- *Stipules.*—Short.
- *Glands.*—Many; normal.
- *Texture.*—Unusually thick but smooth.
- *Edge.*—Finely serrated.

Blossoms:
- *Season.*—Blooms quite early—about same as Elberta.
- *Color.*—Rich pink.
- *Size.*—About the same as Hale and Elberta.

Productiveness: Unusually heavy producer, producing about three times the weight of usual peach tree of same age.
Hardiness: Where tested, it has proved hardy.
Ripening dates of fruit: October 1 to 10 in this climate.

*The fruit*

Size: About the same size as Hale by measurement, but more dense therefore heavier.
Form: Nearly globular, like Hale.
Suture: Slight depression on stem end.
Cavity: Slight.
Stem: Short and stout.
Skin:
- *Texture.*—Medium.
- *Tenacity.*—Quite free and does not split.
- *Fuzz.*—Scant.
- *Color.*—Basic color is cream, which is brightly colored with shades of red and pink, particularly on the stem end.

Flesh:
- *Color.*—Very pronounced pearl white with pink to red shadings extending from the pit.
- *Texture.*—Firm but juicy, without fibres.
- *Flavor.*—Distinctive. Pleasant combination of sweet and tart.
- *Aroma.*—Medium and pleasing.
- *Ripening.*—Even.

Stone: Free.
- *Size.*—Medium—about two-thirds the size of Elberta seed; small to average thickness.
- *Color.*—Reddish.
- *Surface.*—Quite smooth, with ridges and pits under average.
- *Tendency to split.*—None.

Keeping and shipping quality: None superior. As an example, I gathered peaches on October 1st which were eating ripe, put them in a desk drawer in my living room. A week later they were still so sound that they could have been shipped across the continent without icing and have been good for market a week or more.

Resistance to insects and disease: Apparently very resistant, since none have occurred.

Having thus disclosed my discovery, I claim;

The new and distinct variety of free stone peach tree, substantially as herein disclosed, characterized particularly by its vigorous and dense growth, its early bearing and heavy producing qualities; its vigor indicating longevity; its late ripening season; its unusual leaf; and its fruit having scant fuzz, excellent keeping and shipping qualities and pearl white flesh of unusual denseness and lack of fibre.

LAWRENCE W. SHERWOOD.

No references cited.